United States Patent [19]

Weinstock

[11] 4,171,359
[45] Oct. 16, 1979

[54] BENZ-TETRASUBSTITUTED 1-PHENYL-2,3,4,5-TETRAHYDRO-1H-3-BENZAZEPINES

[75] Inventor: Joseph Weinstock, Phoenixville, Pa.

[73] Assignee: SmithKline Corporation, Philadelphia, Pa.

[21] Appl. No.: 895,700

[22] Filed: Apr. 12, 1978

[51] Int. Cl.² ............... A61K 31/55; C07D 223/16
[52] U.S. Cl. ............... 424/244; 260/239 BB; 260/347.2; 260/347.4; 260/347.7; 260/330.3
[58] Field of Search .......... 260/239 BB, 346.1, 329 F; 424/244

[56] References Cited

U.S. PATENT DOCUMENTS 3,496,166  2/1970  Mull et al. ............... 260/239 BB

FOREIGN PATENT DOCUMENTS 555831  11/1974  Switzerland ............... 260/239 BB
1225053  3/1971  United Kingdom ............... 260/239 BB

*Primary Examiner*—Donald G. Daus
*Assistant Examiner*—D. B. Springer
*Attorney, Agent, or Firm*—William H. Edgerton

[57] ABSTRACT

A group of 6,9-disubstituted-7,8-dihydroxy-1-phenyl-2,3,4,5-tetrahydro-1H-3-benzazepines have dopaminergic activity. Examples of leading species of the invention are 6,9-dichloro-7,8-dihydroxy-1-phenyl-2,3,4,5-tetrahydro-1H-3-benzazepine and 6,9-dichloro-7,8-dihydroxy-1-(p-hydroxy-phenyl)-2,3,4,5-tetrahydro-1H-3-benzazepine in the form of an acid addition salt.

16 Claims, No Drawings

BENZ-TETRASUBSTITUTED 1-PHENYL-2,3,4,5-TETRAHYDRO-1H-3-BENZAZEPINES

This invention comprises a new group of compounds which are 1-phenyl-2,3,4,5-tetrahydro-1H-3-benzazepines having at least four substituents in the benz-ring of the nucleus two of which are hydroxy substituents at the 7 and 8 positions and two of which are selected halo or lower alkyl substituents at the 6 and 9 positions. These compounds have utility as medicinally active compounds especially as cardiovascular agents due to their selective peripheral dopaminergic activity.

PRIOR ART STATEMENT

A number of prior art publications and patents disclose variously substituted 1-phenyltetrahydro-1H-3-benzazepines. Many of these have been cited in my corelative applications. Most pertinent to the invention here claimed are the disclosures of Swiss Pat. No. 555,831 and U.S. Pat. No. 4,011,319. The former discloses generically benz-trisubstituted benzazepines but no specific compounds of this class, no 6-halo compounds and no dopaminergic activity. The latter discloses peripheral dopaminergic activity for certain benz-mono and disubstituted benzazepines.

The compounds of this invention are illustrated by the following structural formula:

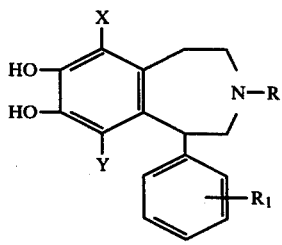

in which X and Y are each halo especially chloro, bromo or fluoro or lower alkyl of 1–4 carbons especially methyl, ethyl, propyl or butyl; R is hydrogen, methyl, ethyl, allyl, dimethylallyl, thenyl or furylmethyl; and $R_1$ is hydrogen, methoxy, hydroxy, acetoxy, halo, trifluoromethyl, methyl or methylthio.

Preferred compounds are those of Formula I in which R is hydrogen. Another subgeneric group comprises the compounds of Formula I in which X and Y are both chloro or methyl; R is hydrogen and $R_1$ is hydrogen, m-hydroxy, p-hydroxy or m-methyl.

The pharmaceutically acceptable acid addition salts having the utility of the free bases of formula I, prepared by methods well known to the art, are formed with both inorganic or organic acids, for example: maleic, fumaric, benzoic, ascorbic, pamoic, succinic, bismethylene-salicyclic, methanesulfonic ethanedisulfonic, acetic, oxalic, propionic, tartaric, salicyclic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. The hydrohalic and methanesulfonic acid salts are especially useful.

Also included in this invention are any metabolic products of or derivatives which are converted in vivo to the compounds of this invention. Such may be the 7,8-dilower alkanoyl derivatives such as those derived from lower alkanoic acids of 2–7 carbons for example diacetoxy, di-isobutyryloxy, di-isovaleryloxy, dipropionyloxy derivatives. These often have enhanced oral activity and would be expected to be utilized to provide a longer duration of activity than the parent diols.

It will be obvious to one skilled in the art that the compounds of Formula I may be present as diastereoisomers which may be resolved into d, l optical isomers. Resolution of the optical isomers may be conveniently accomplished by fractional crystallization of their salts with optically active acids from appropriate solvents. Examples of this procedure are described in Swiss Pat. No. 555,831. Unless otherwise specified herein or in the claims, it is intended to include all isomers, whether separated or mixtures thereof. Where isomers are separated, the desired pharmacological activity will usually predominate in one of the isomers.

The compounds of Formula I are generally prepared from intermediates of the following formula:

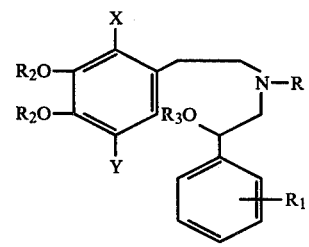

in which X and Y are each halo especially chloro or fluoro or lower alkyl of 1–4 carbons especially methyl, ethyl or propyl; both $R_2$ groups are benzyl, lower alkyl especially methyl or together methylene; $R_3$ is hydrogen or a functionally equivalent group satisfactory for generating a carbonium ion at the α-position of the phenethanolamine moiety; and R and $R_1$ are hydrogen or a chemically inert substituent of the group defined for Formula I, by means of an intramolecular cyclization effected by reaction with a reagent such as sulfuric acid alone or mixed with suitable solvents such as trifluoroacetic acid, polyphosphoric acid or a similar dehydrating agent.

The secondary amine intermediates of Formula II above are conveniently prepared by heating equimolar amounts of a styrene oxide with a 3,4-dialkoxyphenethyl-amine (III) each appropriately substituted, either alone or in an inert organic solvent such as tetrahydrofuran. Preferably the heating is effected on a steam bath or at reflux temperature for from 12 to 24 hours. The required styrene oxide is conveniently prepared by reaction of the ylide derivative from sodium hydride and trimethylsulfonium iodide with the appropriately substituted benzaldehyde. Other preparations of the secondary amines will be apparent from the examples presented hereafter.

The primary amines, i.e. the 2,5-disubstituted-3,4-dialkoxyphenethylamines (III), are not reported in the literature to the best of my knowledge. The methods of the prior art for preparing 1-phenyl-2,3,4,5-tetrahydro-1H-3-benzazepines therefore cannot be used without access to the proper starting materials.

These tetrasubstituted phenethylamines are prepared from catechol by inserting the halogens in the ortho positions or methyl groups by a Mannich reaction-reduction. After O-methylation the amino ethyl group is inserted via chloromethylation-cyanide-reduction sequence of steps or a Mannich reaction-reduction sequence if appropriate. The protective ether groups may be added whenever appropriate. The secondary amines are then prepared from the phenethylamines as described above.

In certain cases such as when the cyclization may proceed with difficulty or when the starting material is not easily prepared it may be advantageous to insert the 6,9-substituents directly into the formed 7,8-dihydroxy-1-phenyl-2,3,4,5-tetrahydro-1H-3-benzazepine.

One example is 6,9-halogenation when interfering groups are protected. Also the catecholic 7,8-dihydroxy system can be oxidized such as by hypohalite or DDQ (2,3-dichloro-5,6-dicyano-1,4-benzoquinone) to the 7,8-quinone. The appropriate hydrohalide is then added to the sensitive 7,8-quinone system. Alternatively combinations of the total synthetic and insertion methods may be used.

Any protective groups are removed by methods known to the art. For example the 7,8 or 4'-alkoxy containing benzazepines may be split using boron tribromide or hydrogen bromide treatment.

The compounds of Formula I where R is methyl, ethyl, allyl etc. are conveniently prepared from ether protected benzazepines by standard N-alkylation methods such as using reactive lower alkyl halides, acylation-reduction or for the methyl compounds, formic acid/formaldehyde or formaldehyde/catalytic hydrogenation. Treatment of the resulting products with boron tribromide gives the corresponding hydroxy substituted benzazepines.

To prepare the O-alkanoyl derivatives the corresponding 3-benzyl-dihydroxy-3-benzazepine (obtained by N-alkylation of the hydroxybenzazepine with benzyl bromide in the presence of potassium carbonate) is treated with the appropriate alkanoic acid anhydride or chloride, for example acetic anhydride, and the resulting alkanoyloxy substituted benzazepine is then hydrogenated in the presence of palladium-on-carbon to remove the protective benzyl group. The dialkanoyloxy derivatives such as the important 7,8-diacetoxy compounds can also be prepared by direct O-acylation of the proper 7,8-dihydroxy-1-phenyl-2,3,4,5-tetrahydro-1H-3-benzazepine hydrobromide in trifluoroacetic acid at ambient temperature with the anhydride or halide.

The active dopaminergic compounds of this invention used herein stimulate peripheral dopamine receptors, for example they increase renal blood flow and have as an end result hypotensive activity. This renal vasodilator activity of the benzazepine compounds of Formula I is measured in an anesthetized dog. In this pharmacological procedure (see U.S. Pat. No. 4,011,319), a test compound is administered at progressively increasing (3-fold) infusion rates beginning at 0.1 mcg/kg/min up to 810 mcg/kg/min for 5 minutes each to anesthetized normotensive dogs and the following parameters are measured: renal artery blood flow, iliac artery blood flow, arterial blood pressure and heart rate. Results are reported as a percent change, increase or decrease, at time of peak response (from pre-drug controls), and for a significant effect renal blood flow (increase) and renal vascular resistance (decrease) should be approximately 10% or greater. The effect on renal vascular resistance can be calculated from any change in renal blood flow and arterial blood pressure. To confirm the mechanism of action, representative active renal vasodilator compounds are checked for blockade by bulbocapnine which is known to be a specific blocker of renal dopamine receptors. Representative advantageous compounds of Formula I, 6,9-dichloro-7,8-dihydroxy-1-phenyl-2,3,4,5-tetrahydro-1H-3-benzazepine used in the form of its hydrochloride salt, tested by i.v. infusion as described above produced an $ED_{15}$ of 3.5 mcg/kg respectively with little direct effect on systemic blood pressure in normotensive animals. 6,9-Dibromo-7,8-dihydroxy-1-phenyl-2,3,4,5-tetrahydro-1H-3-benzazepine hydrochloride has an $ED_{15}$ of 634 mcg/kg in 4 dogs. $ED_{15}$ therefore is the cumulative dose by infusion which produces a 15% decrease in renal vascular resistance (R=(B.P. in mm/hg/B.F. ml/min)).

The preferred compounds of this invention such as the 6,9-dichloro compound mentioned above also have dampened dopaminergic activity at central receptor sites as measured by testing for anti-Parkinsonism activity using a modified standard pharmacological test procedure reported by Ungerstedt et al., in Brain Research 24, 1970, 485–493. This procedure is based on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in this rate turning model. These compounds directly activate the central dopamine receptors and cause contralateral rotation of the lesioned rat.

Rotational activity is defined as the ability of a compound to produce 500 contralateral rotations during a two-hour period after administration, usually intraperitoneally. The dose corresponding to 500 contralateral rotations per two hours is obtained and assigned as the $RD_{500}$ value.

6,9-Dichloro-7,8-dihydroxy-1-phenyl-2,3,4,5-tetrahydro-1H-3-benzazepine hydrochloride is not sufficiently active in this test at 10 mglkg i.p. to give a $RD_{500}$. It in fact gave 496±121 rotations. In comparison 6-chloro-7,8-dihydroxy-1-phenyl-2,3,4,5-tetrahydro-1H-3-benzazepine hydrobromide had a $RD_{500}$ of 0.3 mg/kg. Insertion of a fourth substituent at position 9 therefore produced a compound 30 times less active at central receptors than is the 6-chloro-7,8-dihydroxy cogener. The lead compound of this invention also has indications in test procedures that it has low pressor activity. Therefore a more specific peripheral dopaminergic activity of the compounds of this invention is evident.

A specific and preferred group of compounds is therefore these of Formula I in which X and Y are each chloro, fluoro, methyl, ethyl or propyl with R being hydrogen which have potent, specific peripheral dopaminergic activity giving increased renal blood flow.

Insertion of the N-substituents into the compounds of Formula I should increase central dopaminergic activity.

The pharmaceutical compositions of this invention having dopaminergic activity are prepared in conventional dosage unit forms by incorporating a compound of Formula I, an isomer or a pharmaceutically acceptable acid addition salt thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 15 mg to about 500 mg of active ingredient per dosage unit preferably from 25–200 mg but this quantity depends on the specific biological activity desired, the activity of the active ingredient, route of administration and the conditions of patient.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier for oral administration is used the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing dopaminergic activity in accordance with this invention comprises administering internally to a subject in need of such activity a compound of Formula I or a pharmaceutically acceptable acid addition salt or ester thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal doses will be administered several times such as two or three times a day with the daily dosage regimen being selected from about 30 mg to about 2 g. When the method described above is carried out dopaminergic activity especially hypotensive activity due to increased renal blood flow is produced with a minimum of side effects.

The following examples are designed solely to illustrate the preparation and use of the compounds of this invention. The temperatures are Centigrade. Other variations of these examples will be obvious to those skilled in the art.

EXAMPLE 1

7,8-Dihydroxy-1-phenyl-2,3,4,5-tetrahydro-1H-3-benzazepine (50 g., .17 mole) was suspended in 500 cc of benzene. Trifluoroacetic anhydride (150 g., .71 mole) was added dropwise rapidly. All the solid dissolved by the time all the anhydride was added. The solution was stirred an additional hour and then the volatiles were stripped off; leaving the N,O,O-tris-trifluoroacetyl derivative as an oil in quantitative yield. This was added directly to 500 cc of methanol and hydrogen chloride gas was bubbled in for a few minutes. The reaction stirred for 2 hours and then the solvent was stripped off, leaving an oil which was triturated in ether to give 49 g (82%) of 7,8-dihydroxy-1-phenyl-3-trifluoroacetyl-2,3,4,5-tetrahydro-1H-3-benzazepine; m.p. 182°–188°.

The N-acyl compound (5.35 g., .015 mole) was suspended in 200 cc of acetic acid. Bromine (1.83 cc, 0.36 mole) was added all at once and the reaction stirred at room temperature 2 hours. It was poured into a beaker containing ice water and sodium bisulfite. The product was extracted from this into ether and was washed with water and then bicarbonate until all the actic acid was removed. The ether was dried and evaporated. The residue was crystallized from ethyl acetate-hexane to give the 6,9-dibromo compound; m.p. 155°–162°, 4.1 g (54%).

This compound (3.0 g., .0059 mole) was dissolved in 100 cc of methanol in a 3 neck flask. 10 cc of 40% sodium hydroxide was put in a pressure compensated addition funnel with an argon inlet tube on top. The flask had a vacuum outlet on it. The entire apparatus was deoxygenated five times by pulling a vacuum and refilling the argon. The alkali solution was added to the solution of dibromo compound and was allowed to stir for ½ hour.

Ethereal hydrogen chloride was then added until the solution was acidic. The entire reaction was stripped down to remove the alcohol and ether. Hot water was added until everything dissolved and then crystallization occurred. 6,9-Dibromo-7,8-dihydroxy-1-phenyl-2,3,4,5-tetrahydro-1H-3-benzazepine hydrochloride was collected and recrystallized from water; 1.24 g (47%), m.p. 205°–207°.

EXAMPLE 2

A mixture of 69 g (0.5 mole) of 3,6-dimethyl catechol [J. Org. Chem. 29 2640 (1964)], 200 ml (266 g, 2.11 moles) of dimethyl sulfate, and 700 ml of 10% sodium hydroxide is refluxed under nitrogen for 1 hour. Then an additional 700 ml of 10% sodium hydroxide is added and the mixture stirred at 25° for 18 hours. The reaction mixture is diluted with water, extracted twice with ether, the ether washed with water and dried. Concentration gives 49 g (59%) of 3,6-dimethylveratrole.

A solution of 41.5 g (0.25 mole) of 3,6-dimethyl-veratrole in 175 ml of glacial acetic acid is treated with 15 g (0.5 mole) of formaldehyde and 20 g (0.55 mole) of anhydrous hydrogen chloride for 8 hours at 30°. The mixture is then poured into 750 ml of water and the product extracted with ether, dried, and the ether removed under vacuum to give the desired 3,6-dimethyl-4-chloromethyl-veratrole.

A solution of 43 g (0.20 mole) of the chloromethyl compound in 220 ml of dimethylsulfoxide was treated with 11.36 g (0.23 mole) of sodium cyanide and the mixture stirred at 50° for 1 hour. The reaction mixture is added to 150 ml of ice and diluted with 650 ml of cold water. The product is extracted with ether which was washed with water, dried, and then concentrated under vacuum to give 2,5-dimethyl-3,4-dimethoxybenzylcyanide.

A mixture of 18.3 g (0.0865 mole) of the nitrile, 1.6 g of Raney nickel catalyst and 170 ml of saturated anhydrous methanolic ammonia is hydrogenated at 50°, 100 p.s.i. of hydrogen gas until hydrogen uptake stopped (about 6 hours). Removal of the catalyst by filtration followed by evaporation gives the 2-(2,5-dimethyl-3,4-dimethoxyphenyl)ethylamine which can be used without further purification.

The phenethylamine (25.7 g, 0.12 mole) is heated to 115° in an oil bath. Styrene oxide (14.4 g., .12 mole) is added and the reaction heated for 1 hour. After cooling to ~30°, 2:1 petroleum ether/acetone is added to dissolve the oil; N-[(2-hydroxy-2-phenylethyl)]-N-[2-(2',5'-dimethyl-3',4'-dimethoxyphenyl)ethyl]amine. The product can be used as the oil or after crystallizing from the ether/acetone mixture.

The hydroxyphenethylamine (10 g) is dissolved in 40 ml of trifluoroacetic acid and 3 ml of concentrated sulfuric acid added. The reaction is refluxed for 2 hours. After cooling, most of the trifluoroacetic acid is stripped off and the residue is poured into water. It is made basic with 10% sodium hydroxide and extracted with ether twice. The dried ether is evaporated to leave a solid; 6,9-dimethyl-7,8-dimethoxy-1-phenyl-2,3,4,5-tetrahydro-1H-3-benzazepine.

The dimethoxy derivative (5 g) is converted to 6,9-dimethyl-7,8-dihydroxy-1-phenyl-2,3,4,5-tetrahydro-1H-3-benzazepine hydrobromide using boron tribromide in methylene chloride at −15°. After standing at room temperature for 3 hours, the solvent is stripped. The residue is treated with cold methanol. Stripping gives the desired compound.

EXAMPLE 3

A slurry of 29.1 g (0.1 mole) of 7,8-dihydroxy-1-phenyl-2,3,4,5-tetrahydro-1H-3-benzazepine hydrochloride in 470 ml of 9 N hydrochloric acid at 28° was treated with 329 ml of 5% sodium hypochlorite solution dropwise over 40 minutes while cooling to maintain the reaction temperature at <30°. Stirring was continued for five hours at room temperature. Ten grams of sodium bisulfite was added in several portions over several minutes. After stirring overnight the product was collected by filtration and air-dried to give 33 g of cream-colored powder which was crystallized from water to give analytically pure 6,9-dichloro-7,8-dihydroxy-1-phenyl-2,3,4,5-tetrahydro-1H-3-benzazepine, hydrochloride; m.p. 185°-200° (dec.).

EXAMPLE 4

2-Chloro-3,4-dimethoxyphenethylamine (1.0 g) was reacted with 0.70 g of p-methoxystyrene oxide as described above to give the hydroxyphenethylamine; m.p. 118.5°-121°. This compound (2.16 g) was stirred at room temperature in 15 ml of trifluoroacetic acid with 4 drops of conc. sulfuric acid. Working up as described gave, after purification over a silica gel column with chloroform, 10% methanol/chloroform as eluates, the desired 6-chloro-7,8-dimethoxy-1-p-methoxyphenyl-2,3,4,5-tetrahydro-1H-3-benzazepine (0.78 g), m.p. 143°-145°.

The trimethoxy product (0.87 g, 2.50 mmoles) in 25 ml of dry methylene chloride was cooled in an ice-methanol bath as 12.5 ml (25.0 mmoles) of boron tribromide in methylene chloride was added dropwise. After stirring for 4 hours, the mixture was cooled in an ice bath while methanol was carefully added to give 0.37 g, after crystallization from methanol/ethylacetate, of 6-chloro-7,8-dihydroxy-1-p-hydroxyphenyl-2,3,4,5-tetrahydro-1H-3-benzazepine hydrobromide, m.p. 215°. Treatment with base and then methanesulfonic acid gave the methanesulfonate salt, m.p. 272°.

A solution of 402 mg (1.0 mmole) of the methanesulfonate salt in 12 ml of methanol and 4 ml of conc. hydrochloric acid was treated with a solution of 251 mg (1.1 mmole) of 2,3-dichloro-5,6-dicyano-1,4-benzoquinone (DDQ) in 2 cc of methanol at room temperature. After stirring overnight the reaction was treated with aqueous sodium bisulfite until the red color was discharged. The solution was concentrated in vacuo to about ¼ volume. The tan precipitate was collected by filtration and air-drying to give 430 mg of 6,9-dichloro-7,8-dihydroxy-1-(p-hydroxyphenyl)-2,3,4,5-tetrahydro-1H-3-benzazepine, hydrochloride; m.p. 220°-225° (dec.).

EXAMPLE 5

Substituting a stoichiometric quantity of 2-fluoro-3,4-dimethoxyphenethylamine in the synthetic procedure of Example 4 gave 6-fluoro-7,8-dimethoxy-1-(p-methoxyphenyl)-2,3,4,5-tetrahydro-1H-3-benzazepine as a yellow oil. Hydrolysis with boron tribromide gave 6-fluoro-7,8-dihydroxy-1-(p-hydroxyphenyl)-2,3,4,5-tetrahydro-1H-3-benzazepine hydrobromide, m.p. 277° (dec.). DDQ and hydrochloric acid treatment as in Example 4 gives 9-chloro-6-fluoro-7,8-dihydroxy-1-p-hydroxyphenyl)-2,3,4,5-tetrahydro-1H-3-benzazepine hydrochloride. Substituting appropriate bromo starting material in the methods described in Example 4 gave 6-bromo-7,8-dimethoxy-1-(p-methoxyphenyl)-2,3,4,5-tetrahydro-1H-3-benzazepine then hydrolysis with boron tribromide gave 6-bromo-7,8-dihydroxy-1-(p-hydroxyphenyl)-2,3,4,5-tetrahydro-1H-3-benzazepine hydrobromide, m.p. 254° (dec.). This compound (1.0 mmole) is treated with DDQ-hydrobromic acid to give 6,9-dibromo-7,8-dihydroxy-1-(p-hydroxyphenyl)-2,3,4,5-tetrahydro-1H-3-benzazepine hydrobromide.

EXAMPLE 6

Submitting each of the following compounds disclosed in U.S. Pat. Nos. 4,052,506 or 4,011,319 to the hypochlorite treatment of Example 3 give the corresponding 6,9-dichloro compounds of this invention;

7,8-dihydroxy-1-(3-trifluoromethylphenyl)-2,3,4,5-tetrahydro-1H-3-benzazepine hydrobromide gives 6,9-dichloro-7,8-dihydroxy-1-(3-trifluoromethylphenyl)-2,3,4,5-tetrahydro-1H-3-benzazepine hydrochloride 7,8-dihydroxy-3-ethyl-1-phenyl-2,3,4,5-tetrahydro-1H-3-benzazepine hydrobromide gives 6,9-dichloro-7,8-dihydroxy-3-ethyl-1-phenyl-2,3,4,5-tetrahydro-1H-3-benzazepine hydrochloride 1-(p-chlorophenyl)-7,8-dihydroxy-2,3,4,5-tetrahydro-1H-3-benzazepine hydrobromide gives 6,9-dichloro-7,8-dihydroxy-1-(p-chlorophenyl)-2,3,4,5-tetrahydro-1H-3-benzazepine hydrochloride.

Other substituted 1-phenyl containing compounds can be similarly prepared.

EXAMPLE 7

A mixture of 4 g of 6,9-dichloro-7,8-dimethoxy-1-phenyl-2,3,4,5-tetrahydro-1H-3-benzazepine in 15 ml of formic acid and 10 ml of formaldehyde is refluxed for 18 hours. The mixture is evaporated in vacuo. The residue is treated with 20 ml of 6 N hydrochloric acid. The solution is again evaporated to give a residue which is treated with 20 ml of 10% sodium hydroxide solution then taken into ether. The ethereal extracts are dried and evaporated to give 6,9-dichloro-7,8-dimethoxy-3-methyl-1-phenyl-2,3,4,5-tetrahydro-1H-3-benzazepine.

This material (1.3 g) in 75 ml of methylene chloride is treated with 3.2 g of boron tribromide at −10°. Working up as described above gives 6,9-dichloro-7,8-dihydroxy-3-methyl-2,3,4,5-tetrahydro-1H-3-benzazepine hydrochloride.

An alternative N-methylation comprises N-formylation of the 6,9-dichloro 7,8-dihydroxy compound of Example 3 with catalytic hydrogenation. For example, the starting material is reacted with formaldehyde in methylene chloride with palladium-on-charcoal under low pressure hydrogenation conditions. After absorption of hydrogen, the catalyst is removed and the solvent evaporated.

Substituting N-acylation with thenoyl chloride or α-furylacetyl chloride followed by reduction gives the 3-thenyl or α-furyl methyl compounds. Using allyl bromide with the dihydroxydichloro compound with an excess of potassium carbonate in acetone-methanol in the cold, then stirring at room temperature gives 3-allyl-6,9-dichloro-7,8-dihydroxy-1-phenyl-2,3,4,5-tetrahydro-1H-3-benzazepine hydrochloride.

EXAMPLE 8

A solution of 540 g (containing 500 g) of 4-methoxystyrene in 2 l. of methylene chloride was cooled to −10° and 521.2 g of bromine added dropwise keeping the temperature between −5° and −10°. The last drop caused an abrupt change in color and the addition of bromine was stopped. The solvent was immediately removed under vacuum keeping the bath temperature below 35° and feeding the reaction solution in slowly. When the methylene chloride was gone and the warm oil was mixed with 1600 ml (5.5 ml/g product) of hexane to dissolve the remaining product in the evaporation flask and the bulk of the product. This required warming the solution on a steam bath. Charcoal was added, the solution filtered and the resulting pale yellow solution chilled in an ice bath to give 637 g (58.2% based on styrene, 66% based on bromine uptake) of crystals, m.p. 74°–78°. The pure 1-(4-methoxyphenyl)-1,2-dibromoethane melts 80°–81°.

About 100 ml of liquid was distilled from 600 ml of t-butyl alcohol. To the slightly cooled contents were added 15 g of anhydrous powdered magnesium sulfate. The suspension was stirred for 15 minutes and then 100 g of the dibromoethane added. The reaction was refluxed with stirring for 1.5 hours. About 200 ml of methylene chloride was added to the cooled reaction mixture and the solids were removed by filtration. The solids were washed thoroughly with methylene chloride; the washings were combined with the filtrate and concentrated to dryness at 60° C. The residue was stirred with 500 ml of pentane and 500 ml of water and the layers separated. The organic layer was washed with 5% sodium bicarbonate, dried and concentrated under vacuum to give 91.7 g (94%) of a tan oil; 2-bromo-1-(t-butoxy)-1-(4-methoxyphenyl)ethane.

2-(3,4-Dimethoxy-5-methylphenyl)ethylamine (43.1 g, 0.22 mole) prepared as in J. Knabe et al., Archiv. der Pharmazie, 296 650 (1963), the above bromoethane (57.4 g, 0.2 mole), sodium carbonate (25.2 g, 0.3 mole), and dimethylformamide are heated with stirring under nitrogen for 2 hours at 140°. The reaction mixture is poured into water, extracted with methylene chloride, and the organic layer washed twice with water. The organic layer is then washed twice with 1 N aqueous hydrochloric acid, then with 10% aqueous sodium carbonate, and finally with saturated saline. Drying and concentration gives a brown oil which was treated with 400 ml of 10% sulfuric acid with vigorous stirring for 30 minutes. The reaction mixture after cooling is made basic with 40% sodium hydroxide and then extracted twice with dichloromethane. The organic layer is washed with water, dried, and concentrated to give the desired N-[2-(3,4-dimethoxy-5-methylphenyl)ethyl]-2-(4′-methoxyphenyl)-2-hydroxyethylamine.

The above amino alcohol (69 g, 0.20 mole) is dissolved in 520 ml of trifluoroacetic acid, and to the solution at 25° is added 29.4 g (0.30 mole) of conc. sulfuric acid keeping the solution at 25°. The mixture is stirred at 25° for 3.5 hours and then 74 g, 0.90 mole of sodium acetate is added with cooling. The reaction mixture is concentrated under vacuum to remove the trifluoroacetic acid, water followed by ammonium hydroxide is added (pH 11), and the suspension extracted with methylene chloride. Concentration gives a solid which is purified by recrystallization; 9-methyl-7,8-dimethoxy-1-(4′-methoxyphenyl)-2,3,4,5-tetrahydro-1H-3-benzazepine.

A mixture of 21.6 (0.066 mole) of the trimethoxybenzazepine, 82.5 g (0.33 mole) of boron tribromide, and 216 ml of methylene chloride is allowed to react at 15° for 1 hour and 3 hours at 25°. Then 165 ml of methanol is added keeping the reaction temperature at −20°. The temperature is slowly brought to 25°, and the slurry concentrated under vacuum until most of the volatile material is gone. The residue is triturated with 100 ml of ethyl acetate, and the crystalline product collected and washed with ether. This gives 9-methyl-7,8-dihydroxy-1-(4′-hydroxyphenyl)-2,3,4,5-tetrahydro-1H-3-benzazepine hydrobromide. The free base is obtained by stirring with 2 moles of sodium bicarbonate in water, filtering, and washing well with water. It may be converted to the hydrochloride or methane sulfonate salts by treating a methanol suspension of the free base with a 20% excess of the appropriate acid, adding excess ethyl acetate to precipitate the product, chilling, filtering, and then washing with ethyl acetate.

To a suspension of 32.2 g (0.1 mole) of the hydrochloride of the above benzazepine in 275 ml of methanol at 0° under argon is added a solution of 25.2 g (0.111 mole) of 2,3-dichloro-5,6-dicyano-1,4-benzoquinone rapidly. After stirring for 1 hour at 0°, the reaction mixture is filtered and the solid washed with 75 ml of cold methanol, 100 ml of ethyl acetate and 100 ml of ether. The product is the 7,8-dione of the initial benzazepine. A stirred suspension of 4.8 g (0.015 mole) of the 7,8-dione in 150 ml of methanol is treated with an excess of dry HCl. Concentration gives the 1-(4′-hydroxyphenyl)-7,8-dihydroxy-6-chloro-9-methyl-2,3,4,5-tetrahydro-1H-3-benzazepine hydrochloride which may be recrystallized from methanolethyl acetate.

Oxidation of the hydrobromide salt as described above followed by treatment with hydrobromic acid gives the 6-bromo-hydrobromide analog.

1-Phenyl-7,8-dihydroxy-9-methyl-2,3,4,5-tetrahydro-1H-3-benzazepine is obtained by treating 2-(3,4-dimethoxy-5-methylphenyl)ethylamine in tetrahydrofuran with styrene oxide for 12 hours as described above to give N-[(2-hydroxy-2-phenylethyl)]-2-(3′,4′-dimethoxy-5-methylphenyl)ethylamine which on cyclization gives the 7,8-dimethoxy benzazepine. Cleavage of this as described gives the desired 6-methyl compound as the hydrobromide which may be converted via the free base to the hydrochloride.

Oxidation with DDQ in methanol with hydrochloric acid gives 6-chloro-9-methyl-1-phenyl-7,8-dihydroxy-2,3,4,5-tetrahydro-1H-3-benzazepine hydrochloride.

EXAMPLE 9

Isovanillin (76.1 g, 0.5 m) was suspended in 750 ml of chloroform. Bromine (27.3 ml, 0.5 m) in 200 ml of chloroform was added at 0° slowly. Water was added to give the desired 2-bromo-3-hydroxy-4-methoxybenzaldehyde, m.p. 197°–203°.

The aldehyde product (46.2 g, 0.2 mole) was dissolved in 300 ml of dry dimethylformamide, 69.1 g of potassium carbonate was added. 28.4 ml (0.30 mole) of dimethylsulfate was added at room temperature dropwise. After the addition the reaction was heated on the stream bath for 10 minutes. 29 Ml of water was added dropwise and the reaction again heated for 5 minutes on the steam bath. The reaction was then poured into ice water and the precipitate collected, 2-bromo-3,4-dimethoxybenzaldehyde, m.p. 80°–81.5°.

The dimethoxybenzaldehyde (10 g, 0.04 mole) was dissolved in 100 ml of ethanol 5 g (0.132 mole) of sodium borohydride was added. The reaction was stirred for 1 hour. The reaction mixture was poured into water and extracted into methylene chloride to give tne benzyl alcohol (m.p. 74°–76.5°). This was converted to the benzyl chloride as a tan liquid, using benzene and conc. hydrochloric acid then to the benzyl cyanide, m.p. 48°–55° using sodium cyanide in dimethylsulfoxide.

The benzyl cyanide (8.05 g. 0.315 mole) was dissolved in 80 ml of dry tetrahydrofuran and then added slowly to 80 ml of 1 M boron trifluoride in tetrahydrofuran at 5°. After refluxing for 2 hours, the mixture was cooled and 40 ml of methanol added carefully. After refluxing shortly and standing overnight the mixture was concentrated to give a tan oil. Dilute hydrochloric acid was added. The material was washed with ether, filtered and the filtrate made basic with 40% sodium hydroxide. After extracting with ether, washing, drying and evaporated the extracts the desired phenethylamine was obtained as a viscous, light yellow oil.

The phenethylamine (0.12 mole) is heated to 115° in an oil bath. Styrene oxide (14.4 g, 0.12 mole) is added and the reaction heated for 1 hour. After cooling to ~30°, 2:1 petroleum ether/acetone is added to give N-[(2-hydroxy-2-phenylethyl)]-N-[2-(2'-bromo-3', 4'-dimethoxyphenyl)ethyl]amine.

The hydroxyphenethylamine (0.0445 mole) is dissolved in 60 ml of trifluoroacetic acid and 4.05 ml of concentrated sulfuric acid is added. The reaction is refluxed for 2 hours. After cooling most of the trifluoroacetic acid is stripped off and the residue is poured into water. It is made basic with 10% sodium hydroxide and extracted with ether twice. The ether is dried and evaporated to give 6-bromo-7,8-dimethoxy-1-phenyl-2,3,4,5-tetrahydro-1H-3-benzazepine.

Using this general procedure with variously substituted styrene oxides having one or more methyl, methoxy, methylthio, trifluoromethyl groups gives the corresponding 6-bromo intermediates not readily prepared by direct bromination which are used for preparing the 6-alkyl derived compounds of this invention by the methods described hereafter.

The 6-bromo-7,8-dimethoxy compound (100 g) in a large excess of ethyl formate is heated at reflux for 10 hours. Evaporation in vacuo and purification by fractional recrystallization give the 3- or N-formyl derivative.

6-Bromo-3-formyl-7,8-dimethoxy-1-phenyl-2,3,4,5-tetrahydro-1H-3-benzazepine (82.6 g, 0.212 mole) was dissolved in 1500 ml of toluene and added to a mixture of 0.678 mole of n-butyl lithium, 250 ml of toluene and 250 ml of ether at −78°. After addition, the mixture was stirred for 10 minutes. N-Methylformanilide (86 g, 0.636 mole) was added to the mixture followed by stirring at −78° for 1 hour. The cooling bath was removed and 500 ml of 10% hydrochloric acid and 250 ml of water were added to give the 6-formyl derivative as the hydrochloride salt, m.p. 209°–210°, after standing overnight. This material is N-formylated in an excess of ethyl formate at reflux for 6 hours.

The 3,6 -diformyl-7,8-dimethoxy product was reacted with a slight excess of ethyl lithium in ethyl ether at 0°–5° to give 7,8-dimethoxy-6-α-hydroxypropyl-1-phenyl-2,3,4,5-tetrahydro-1H-3-benzazepine.

A mixture of 7.5 g of 7,8-dimethoxy-6-α-hydroxypropyl-1-phenyl-2,3,4,5-tetrahydro-1H-3-benzazepine in 500 ml of ethylformate was heated at reflux for 5 hours then worked up using medium pressure liquid chromatography to give the N-formyl derivative.

This material (4.9 g) in 150 ml of chloroform and 50 ml of concentrated hydrochloric acid was heated at reflux for 2 hours. A small amount of aldehyde by-product was removed by bisulfite extraction to give the 6-α-chloropropyl compound.

This material (3.6 g) in dry dimethylsulfoxide was added dropwise to a solution of 1.07 (0.028 mole) of sodium borohydride in dry dimethylsulfoxide. After stirring at room temperature the mixture was heated on the steam bath for several hours then poured into water. The product was taken into ethyl ether-ethyl acetate and purified by chromatography using methanol-chloroform to give 3-formyl-7,8-dimethoxy-6-propyl-1-phenyl-2,3,4,5-tetrahydro-1H-3-benzazepine.

This material (1.9 g, 0.0054 mole) in 50 ml of ethanol and 10 ml of 40% sodium hydroxide was heated at reflux for 2 hours. After stripping, the residue was taken up in methylene chloride-water. The combined organic layers were dried and evaporated to give the 7,8-dimethoxy compound which (1 g) was reacted with 1 ml of boron tribromide in dry methylene chloride for 3 hours. After stripping and cooling the residue was treated with methanol. The methanol was taken off and the residue dissolved in hot water (20 ml). Evaporation and cooling gave the dopaminergic agent 7,8-dihydroxy-6-n-propyl-1-phenyl-2,3,4,5-tetrahydro-1H-3-benzazepine hydrobromide, m.p. 226°–229°.

The 6-propyl-7,8-dihydroxy compound is oxidized with DDQ to the 7,8-quinone then treated with hydrochloric acid as in Example 7 to give 9-chloro-6-n-propyl-7,8-dihydroxy-1-phenyl-2,3,4,5-tetrahydro-1H-3-benzazepine hydrochloride.

EXAMPLE 10

6-Formyl-7,8-dimethoxy-1-phenyl-2,3,4,5-tetrahydro-1H-3-benzazepine hydrochloride (6.3 g, 0.018 mole) from Example 9 was converted to the free base by aqueous alkali and methylene chloride. The organic layer was dried with magnesium sulfate and evaporated. The residue was refluxed in 500 ml of ethyl formate for 2 hours. The excess formate was distilled off and the residue was dissolved in ethyl acetate and extracted once with dil. hydrochloric acid. Drying and evaporation left 3,6-diformyl-7,8-dimethoxy-1-phenyl-2,3,4,5-tetrahydro-1H-3-benzazepine.

This compound (6.1 g, 0.018 mole) was dissolved in 50 ml of isopropanol. Solid sodium borohydride was added slowly until 1.33 g (0.036 mole) had been added. The reaction stirred at room temperature for 2 hours, then worked up by the careful addition of water, then dil. hydrochloric acid to the cooled solution. When the solution was acidic, the isopropanol was stripped off. Water and ether were added to the residue to dissolve it. The ethereal layer was washed with bicarbonate, dried and evaporated to give an oily 3-formyl-7,8-dimethoxy-6-hydroxymethyl-1-phenyl-2,3,4,5-tetrahydro-1H-3-benzazepine.

The oil (~4 g) was dissolved in 50 ml of ethanol and 10 ml of 40% sodium hydroxide was added. The reaction was heated at reflux for 1½ hours. The ethanol was stripped off and the residue dissolved in ether and water. The ether layer was washed again with water and dried. The solution was acidified with ethereal hydrogen chloride. The solid was separated by decanting the supernatant liquors. The residue was crystallized from methanol-ethylacetate to give 6-methyl-7,8-dimethoxy-1-phenyl-2,3,4,5-tetrahydro-1H-3-benzazepine hydrochloride, m.p. 223°–227°.

The dimethoxy compound (3.1 g, 0.0093 mole) was converted to the free base with alkali-methylene chloride. The organic layer was washed with water and dried, then was cooled to −15° at which time 3 ml of boron tribromide was added. The reaction stirred 3½ hours at room temperature. The volatiles were stripped off and after cooling to −15°, methanol was added until the solid dissolved. The methanol was evaporated and the residue was dissolved in boiling water. The solution was treated with activated charcoal and filtered while hot. Crystallization of the hot solution gave 1.2 g of 6-methyl-7,8-dihydroxy-1-phenyl-2,3,4,5-tetrahydro-1H-3-benzazepine hydrobromide, m.p. 160°–163°. The base and methylsulfonate salt are prepared as described above.

This compound is oxidized to the 7,8-quinone with DDQ then the 7,8-dione is reacted with hydrochloric acid as above to give 9-chloro-6-methyl-7,8-dihydroxy-1-phenyl-2,3,4,5-tetrahydro-1H-3-benzazepine hydrochloride.

EXAMPLE 11

A 4.0 g sample of 3-benzyl-6,9-dimethyl-7,8-dihydroxy-1-phenyl-2,3,4,5-tetrahydro-1H-3-benzazepine (prepared from the 3-unsubstituted benzazepine by reaction with benzyl bromide in the presence of potassium carbonate) is dissolved in 50 ml of acetic anhydride and the solution is heated on a steam bath for one hour. The reaction mixture is cooled, ice-water is added and the solution is evaporated to dryness. The residue is triturated with ethyl acetate, the solution washed with water, dried and the solvent removed in vacuo to leave an oil. The latter is dissolved in ether and ethereal hydrogen chloride is added to precipitate 3-benzyl-6,9-dimethyl-7,8-diacetoxy-1-phenyl-2,3,4,5-tetrahydro-1H-3-benzazepine hydrochloride.

The diacetoxy compound prepared above, 3.5 g is dissolved in 100 ml of ethanol and 1 g of 10% palladium-on-carbon is added. The mixture is hydrogenated in a Parr apparatus at 50° under 50 psi of hydrogen for one hour. The reaction mixture is filtered and the filtrate is evaporated to give 6,9-dimethyl-7,8-diacetoxy-1-phenyl-2,3,4,5-tetrahydro-1H-3-benzazepine hydrochloride.

Alternatively 6,9-dichloro-7,8-dihydroxy-1-phenyl-2,3,4,5-tetrahydro-1H-3-benzazepine hydrobromide (10 g) is dissolved in trifluoroacetic acid and reacted with a stoichiometric amount of acetyl chloride at room temperature. The next day the reaction mixture is evaporated and the residue recrystallized to give the desired diacetoxy derivative.

Substituting other alkanoyl anhydrides or chlorides gives various 7,8-alkanoyl derivatives.

EXAMPLE 12

1,2,3,4-Tetrafluorobenzene (67.7 g), sodium hydrobromide (20.8 g), and 200 ml of ethyleneglycol are refluxed with good stirring for 3 hours. The reaction mixture is poured into water (800 ml), acidified with 10% hydrochloric acid and then extracted with ether. The ether is washed with dilute sodium hydroxide and water, and then distilled under vacuum to give 2-(2,3,6-trifluorophenoxy) ethanol), b.p. about 100° at 15 min.

2-(2,3,6-Trifluorophenoxy) ethanol (48.8 g, 0.254 mole) and 24 g of anhydrous potassium carbonate in 800 ml of dimethylformamide was refluxed for 20 hours and then poured into water. This was extracted with ether, washed with water, and dried to give 5,8-difluoro-1,4-benzodioxane.

5,8-Difluoro-1,4-benzodioxane (30.6 g, 0.02 mole) is dissolved in 126 ml of acetic acid, 31.2 ml of 37% formaldehyde aqueous solution is added. Dry hydrogen chloride gas is bubbled in continuously keeping the temperature between 35°–38°. After 4 hours the reaction mixture is poured into water, extracted twice with ether, the extracts washed with water, sodium bicarbonate, and water, and then dried. Concentration gives 6-chloromethyl-5,8-difluoro-1,4-benzodioxane.

6-Chloromethyl-5,8-difluoro-1,4-benzodioxane (36.9 g, 0.183 mole) is dissolved in 500 ml of dimethylsulfoxide and 11.2 g (0.23 mole) of sodium cyanide added. This is stirred at 25° for 1 hour, and then poured into cold water. Extraction with ether, washing the extract with water, drying and concentration gives 6-cyanomethyl-5,8-difluoro-1,4-benzodioxane.

6-Cyanomethyl-5,8-difluoro-1,4-benzodioxane (30.34 g, 0.158 mole) dissolved in 300 ml of dry tetrahydrofuran is treated with 308 ml of 1 M borane in tetrahydrofuran under nitrogen. After 2 hours of reflux 300 ml of methanol is added continuously (hydrogen evolution occurs, vigorously at first), then the mixture is refluxed for 30 minutes. Then 50 ml of 10% hydrochloric acid is added very carefully (hydrogen gas evolution again) and the mixture refluxed another 30 minutes. The reaction mixture is concentrated under vacuum to a small volume, then 300 ml of water is added and the mixture made basic with 40% sodium hydroxide. This is extracted with ether, dried, and concentrated to give 6-(2-aminoethyl)-5,8-difluoro-1,4-benzodioxane.

The primary amine (21 g), 2-bromo-1-(t-butoxy)-1-(4-methoxyphenyl)ethane (25 g), sodium carbonate (12.6 g) and dimethylformamide are mixed and heated at 140° for 3 hours. The mixture is poured into water and extracted with methylene chloride. The organic extracts are washed twice with water, then twice with 1 N hydrochloric acid, 10% sodium carbonate and finally saturated saline. Drying the organic extract and concentrating in vacuo gives a residue which is treated with 200 ml of 10% sulfuric acid with stirring for 30 minutes. The mixture is cooled, made basic with 10% sodium hydroxide then extracted several times with dichloromethane. The combined organic layers are washed with water dried and evaporated to give the secondary amine.

The crude amine (27 g) is dissolved in 300 ml of trifluoroacetic acid and a one-fold molar excess of concentrated sulfuric acid is added at 25°. After stirring for 3 hours, the mixture is mixed with an excess of sodium acetate with cooling. The mixture is concentrated in vacuo to remove the trifluoroacetic acid. Water is added to the residue followed by ammonium hydroxide to pH 11. The suspension is extracted with methylene chloride. The combined extracts are washed, dried and concentrated to give 6,9-difluoro-1-(p-methoxyphenyl)-7,8-dioxyethylene-2,3,4,5-tetrahydro-1H-3-benzazepine.

The ethyleneoxydifluorobenzazepine (12.7 g), 200 ml of 47% hydrogen iodide and 5 ml of hypophosphorous acid is heated at reflux for 6 hours under nitrogen. Cooling gives a solid which is collected, washed with ethyl acetate and ether to give 6,9-difluoro-7,8-dihydroxy-1-(p-hydroxy-phenyl)-2,3,4,5-tetrahydro-1H-3-benzazepine hydroiodide. This compound is converted to the base using sodium carbonate, and the hydrochloride salt prepared as described above.

EXAMPLE 13

| Ingredients | Mg. per Capsule |
|---|---|
| 6,9-Dichloro-7,8-dihydroxy-1-(p-hydroxyphenyl)-2,3,4,5-tetrahydro-1H-3-benzazepine methanesulfonate | 50 (free base) |
| Magnesium stearate | 2 |
| Lactose | 200 |

The above ingredients are thoroughly mixed and placed into hard gelatin capsules. Such capsules are administered orally to subjects in need of treatment from 2-5 times daily to induce peripheral dopaminergic activity to treat hypertension.

EXAMPLE 14

| Ingredients | Mg. per Tablet |
|---|---|
| 6,9-Dichloro-7,8-dihydroxy-1-(p-hydroxyphenyl)-2,3,4,5-tetrahydro-1H-3-benzazepine methanesulfonate | 100 (free base) |
| Corn starch | 30 |
| Polyvinyl pyrrolidone | 12 |
| Corn starch | 16 |
| Magnesium stearate | 3 |

The first two ingredients are thoroughly mixed and granulated. The granules obtained are dried, mixed with the remaining corn starch and magnesium stearate, and compressed into scored tablets which can optionally be broken in two for 50 mg dosages.

Sustained release capsules may be prepared by using the methods of U.S. Pat. No. 2,738,303. Of course one such capsule may replace several conventional tablets or capsules.

The capsules or tablets thusly prepared are administered orally from 2-5 times daily to an animal or human requiring stimulation of peripheral dopamine receptors within the dose ranges set forth hereinabove. Similarly other compounds of Formula I and the illustrative examples can be formulated in the same manner to give pharmaceutical compositions useful in the methods of this invention based on their chemical characteristics and relative biological activity using the test methods outlined.

What is claimed is:
1. A compound of the formula:

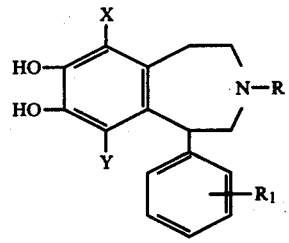

in which:
X and Y are each halo or lower alkyl of 1–4 carbons;
R is hydrogen, methyl, ethyl, allyl, dimethylallyl, thenyl or furylmethyl; and
$R_1$ is hydrogen, methyl, methoxy, hydroxy, acetoxy, halo, trifluoromethyl or methylthio; together with pharmaceutically acceptable nontoxic salts thereof or O-aklkanoyl esters thereof having from 2–7 carbons in each alkanoyl group.

2. The compound of claim 1 in which R is hydrogen.
3. The compound of claim 2 in which $R_1$ is p-hydroxy.
4. The compound of claim 1 in which R is hydrogen and X and Y are both chloro, fluoro or methyl.
5. The compound of claim 4 in which $R_1$ is hydrogen or p-hydroxy.
6. The compound of claim 1 being 6,9-dichloro-7,8-dihydroxy-1-phenyl-2,3,4,5-tetrahydro-1H-3-benzazepine, its hydrohalide or methanesulfonate salts or its O-acetyl esters.
7. The compound of claim 6 has its methanesulfonate salt.
8. The compound of claim 1 being 6,9-dichloro-7,8-dihydroxy-1-(p-hydroxyphenyl)-2,3,4,5-tetrahydro-1H-3-benzazepine, its hydrohalide or methanesulfonate salts or its O-acetyl esters.
9. The compound of claim 1 being 6,9-difluoro-7,8-dihydroxy-1-(p-hydroxyphenyl)-2,3,4,5-tetrahydro-1H-3-benzazepine, its hydrohalide or methanesulfonate salts or its O-acetyl esters.
10. The compound of claim 1 being 6,9-dimethyl-7,8-dihydroxy-1-(p-hydroxyphenyl)-2,3,4,5-tetrahydro-1H-3-benzazepine, its hydrohalide or methanesulfonate salts or its O-acetyl esters.
11. The compound of claim 1 in which X and Y are each a substituent other than bromo.
12. The compound of claim 1 in which X is methyl and Y is chloro.
13. The method of inducing dopaminergic activity in an animal or human subject in need thereof comprising administering orally or by injection a nontoxic dopaminergic quantity of a compound of claim 1, 2, 6, 8, 9 or 10.
14. A pharmaceutical composition for inducing dopaminergic activity comprising a dopaminergic nontoxic quantity of a compound of claims 1, 2, 6, 8, 9 or 10 and a carrier therefor.
15. The composition of claim 14 in which the quantity of compound is selected from the range of about 15–500 mg.
16. The method of claim 13 in which the quantity is an oral dosage unit selected from the range of about 15–500 mg administered from 2–5 times daily.

* * * * *